United States Patent
Ebner et al.

(10) Patent No.: US 9,366,553 B2
(45) Date of Patent: Jun. 14, 2016

(54) AUTOMATED INSERTION OF A CONTACT ROD INTO A METALLURGICAL PROBE

(75) Inventors: Helmut Ebner, Naarn i.M. (AT); Simon Pfeil, Linz (AT); Roger Scheidegger, St. Valentin (AT)

(73) Assignee: PRIMETALS TECHNOLOGIES AUSTRIA GmbH, Linz (AT)

( * ) Notice: Subject to any disclaimer, the term of this patent is extended or adjusted under 35 U.S.C. 154(b) by 250 days.

(21) Appl. No.: 13/985,885

(22) PCT Filed: Dec. 22, 2011

(86) PCT No.: PCT/EP2011/073726
§ 371 (c)(1),
(2), (4) Date: Aug. 16, 2013

(87) PCT Pub. No.: WO2012/110148
PCT Pub. Date: Aug. 23, 2012

(65) Prior Publication Data
US 2013/0312548 A1    Nov. 28, 2013

(30) Foreign Application Priority Data
Feb. 16, 2011   (EP) .................................. 11154627

(51) Int. Cl.
*G01D 11/30*   (2006.01)
*G01K 13/12*   (2006.01)
*G01N 1/12*   (2006.01)

(52) U.S. Cl.
CPC .............. *G01D 11/30* (2013.01); *G01K 13/125* (2013.01); *G01N 1/125* (2013.01); *Y10T 29/49776* (2015.01); *Y10T 29/49826* (2015.01)

(58) Field of Classification Search
CPC ................................ G01D 11/30; F27D 19/00

USPC .............. 73/866.5, 866.4; 374/139–140, 208; 29/248; 376/249
See application file for complete search history.

(56) References Cited

U.S. PATENT DOCUMENTS

| 4,003,261 A | 1/1977 | Nautet et al. |
| 4,204,431 A | 5/1980 | Schulz |

(Continued)

FOREIGN PATENT DOCUMENTS

| CN | 101237822 | 8/2008 |
| CN | 101303370 | 11/2008 |

(Continued)

OTHER PUBLICATIONS

"SIMETAL LiquiRob for EAF: Robot-aided measuring and sampling at EAF," Siemens VAI, www.siemens-vai.com, 2012, 2 pages.

(Continued)

*Primary Examiner* — Peter Macchiarolo
*Assistant Examiner* — Anthony W Megna Fuentes
(74) *Attorney, Agent, or Firm* — Staas & Halsey LLP

(57) ABSTRACT

A metallurgical probe has a probe longitudinal axis and an open end face. The probe is fitted within a bearing point in such a manner that the open end face faces a predetermined insertion direction. The bearing point has probe centering elements to hold the probe in a predetermined probe position as seen transversely with respect to the probe longitudinal axis. A device inserts an end of the contact rod into a contact rod centering device, in an insertion direction running transversely with respect to the probe longitudinal axis, until the end of the contact rod is positioned, on account of the insertion into the contact rod centering device, in a predetermined contact rod position, in which the end of the contact rod is opposite the open end face. The contact rod is then moved in a direction of the probe longitudinal axis and is inserted into the probe.

13 Claims, 7 Drawing Sheets

(56) References Cited

U.S. PATENT DOCUMENTS

| | | | |
|---|---|---|---|
| 4,984,904 A * | 1/1991 | Nakano et al. | 374/139 |
| 7,867,173 B2 | 1/2011 | Hibner et al. | |
| 2012/0082183 A1 | 4/2012 | Beyens | |

FOREIGN PATENT DOCUMENTS

| | | |
|---|---|---|
| CN | 101907587 | 12/2010 |
| DE | 2552270 | 6/1977 |
| EP | 11154627.1 | 2/2011 |
| WO | PCT/EP2011/073726 | 12/2011 |

OTHER PUBLICATIONS

English language copy of International Search Report for PCT/EP2011/073726, mailed Feb. 21, 2012, 2 pages.
Russian Notice of Allowance for related Russian Patent Application No. 2013140970/28(062505), issued on Oct. 8, 2015, 13 pages (including partial German-language translation).
English Abstract of Soviet Reference No. 168495 A1, Published Feb. 18, 1965.

* cited by examiner

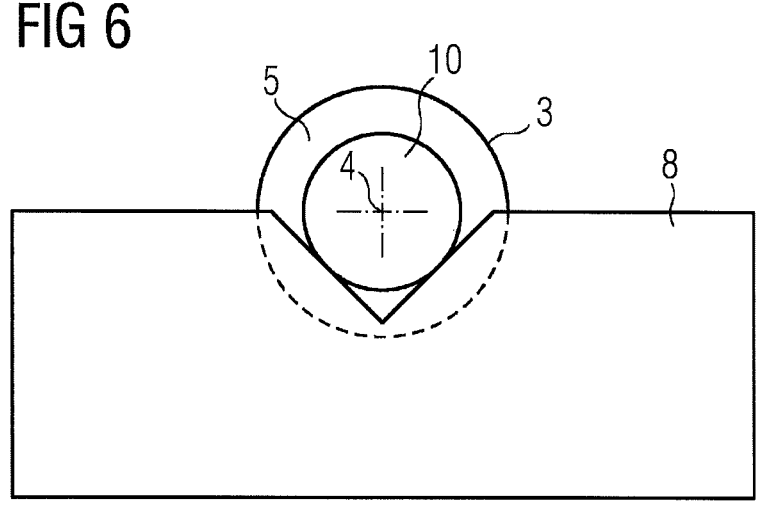
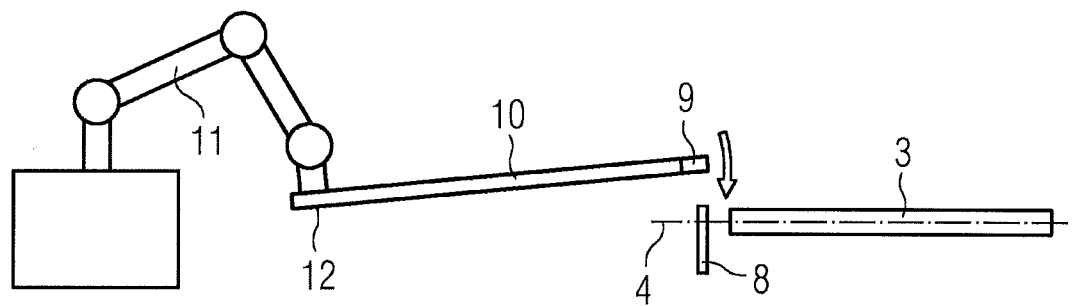

AUTOMATED INSERTION OF A CONTACT ROD INTO A METALLURGICAL PROBE

CROSS REFERENCE TO RELATED APPLICATIONS

This application is based on and hereby claims priority to International Application No. PCT/EP2011/073726 filed on Dec. 22, 2011 and European Application No. 11154627.1 filed on Feb. 16, 2011, the contents of which are hereby incorporated by reference.

BACKGROUND

The present invention relates to a method for inserting a contact rod into a metallurgical probe.

The present invention also relates to a bearing point for a metallurgical probe.

The inventors further propose a holding frame having a plurality of such bearing points.

During the production of iron, steel and other metals, samples of the molten metal are taken, temperatures are measured, etc. For such tasks, metallurgical probes are used which have a probe longitudinal axis and are open on one end face and closed on the other end face. The probes are generally only used once and then disposed of.

In the related art, the probes are connected to a contact rod so that the contact rod is inserted (state) in the probe. The contact rod together with the attached probe is then dipped into the metal melt using a manipulator or robot or similar so that the probe can perform its intended function. The contact rod together with the attached probe is then withdrawn from the melt, after which the probe is removed from the contact rod.

In the related art the known practice is for an operative to remove the probe to be used from a storage container and manually attach it to the contact rod. This is inconvenient, laborious and, on account of the harsh operating conditions in metallurgical plants, to be avoided where possible. An automated solution is therefore desirable. However, there are basically two problems for implementing an automated solution.

On the one hand, when the contact rod is dipped into the metal melt, the rod is often plastically deformed. The degree of plastic deflection can vary. However, due to the fact that the end of the contact rod to be inserted into the probe must be very precisely positioned, even slight deflections are critical in respect of automated insertion of the end of the contact rod into the probe. For example, the contact rod may have a diameter of approximately 16 mm, the probe an inside diameter of approximately 16.5 to 17.0 mm.

On the other hand, the end of the contact rod to be inserted into the probe often oscillates and vibrates, e.g. due to shocks and the more or less jerky movement of large masses. Because of the positioning accuracy required, such oscillations and vibrations also make the automated insertion of the end of the contact rod into the probe considerably more difficult.

In order to enable an automated solution to be implemented nonetheless, it is known in the related art to use a centering device having a contact-rod-side funnel area and a probe-side funnel area which merge at their narrow points. By introducing the end of the contact rod into the contact-rod-side funnel area and introducing the probe into the probe-side funnel area, the end of the contact rod and the open end face of the probe are centered relative to one another, so that the end of the contact rod can be inserted into the probe.

The known centering device must necessarily be openable, as otherwise, although the contact rod, following insertion into the probe, could be withdrawn from the probe again, it could not be removed from the centering device together with the probe. The known centering device must therefore comprise an appropriate actuator system, corresponding moving parts, a power supply and a control device. It is therefore, on the one hand, relatively complex and expensive and, on the other, relatively prone to malfunction on account of the harsh operating conditions in metallurgical plants.

SUMMARY

One potential object is to create a simple way of enabling reliable automatic insertion of the end of the contact rod into the probe.

The inventors propose a method for inserting a contact rod, held in a holding area by a holding and movement apparatus, into a metallurgical probe which has a probe longitudinal axis and is open on an end face wherein a bearing point for the probe is fitted with the probe such that the open end face thereof faces a predetermined insertion direction, wherein the bearing point has probe centering elements by which the probe is held at the bearing point in a predetermined probe position when viewed transversely with respect to the probe longitudinal axis, wherein one end of the contact rod is inserted into a contact rod centering device in an insertion direction running transversely to the probe longitudinal until the end of the contact rod is positioned in a predetermined contact rod position as a result of insertion into the contact rod centering device when viewed transversely with respect to the probe longitudinal axis, in which position the end of the contact rod is opposite the open end face, wherein the contact rod in then moved in the direction of the probe longitudinal axis and is thereby inserted into the probe.

This procedure enables the end of the contact rod to be reliably inserted into the probe, without the need for a complex, actuated, controlled, etc. centering device. Instead, the bearing point can be of purely rigid mechanical design.

In the event of the contact rod being unbent, the contact rod would have to be moved in the insertion direction to an ideal position so that the end of the contact rod is positioned at the predetermined contact rod position when viewed transversely with respect to the probe longitudinal axis as a result of insertion into contact rod centering device. It is possible, for example, for the contact rod to be moved in the insertion direction to beyond the ideal position. Because of such an "overshoot" or "overbending", irrespective of whether or not the contact rod is bent, the end of the contact rod always lies against the contact rod centering device, causing it, on the one hand, to assume the defined position and, on the other hand, suppressing vibrations and oscillations.

Alternatively, an equivalent embodiment is that, during the insertion of the end of the contact rod into the contact rod centering device, a force required for inserting the end of the contact rod is measured and the attainment of the predetermined contact rod position is detected on the basis of said force.

The end of the contact rod can be simply and reliably inserted into the probe due to the fact that, when the contact rod is moved in the direction of the probe longitudinal axis, initially the contact rod is only partially inserted into the probe, the contact rod is then moved out of the predetermined contact rod position counter to the insertion direction, and only thereafter is the contact rod inserted fully into the probe.

Insertability can be facilitated still further if the probe is flared at its open end face before being fitted to the bearing point. The corresponding flaring can in particular be funnel-shaped.

The holding and movement apparatus can be implemented according to requirements. In particular, it can be implemented as a robotic arm.

The inventors also propose a bearing point for a metallurgical probe which has a probe longitudinal axis and is open on an end face,—wherein the bearing point has probe centering elements by which the probe is held at the bearing point in a predetermined probe position when viewed transversely with respect to the probe longitudinal axis, wherein the bearing point has a contact rod centering device into which one end of a contact rod held in a holding area by a holding and movement device can be inserted in an insertion direction running transversely with respect to the probe longitudinal axis until the end of the contact rod is positioned in a predetermined contact rod position when viewed transversely with respect to the probe longitudinal axis as a result of insertion into the contact rod centering device.

In a preferred embodiment of the bearing point, it is provided that the side of the bearing point opposite the contact rod centering device with respect to the probe has a stop for the probe by which the probe is prevented from being displaced in the direction of the probe longitudinal axis.

The inventors further propose a holding frame having a plurality of such bearing points. The bearing points can in particular be arranged in a two-dimensional grid.

BRIEF DESCRIPTION OF THE DRAWINGS

These and other objects and advantages of the present invention will become more apparent and more readily appreciated from the following description of the preferred embodiments, taken in conjunction with the accompanying drawings of which:

FIG. 6 shows a section along a line VI-VI in FIG. 4,

FIG. 8 schematically illustrates the insertion of the end of a contact rod into a contact rod centering device, FIG. 9 schematically illustrates the probe and the contact rod centered relative to the probe.

DETAILED DESCRIPTION OF THE PREFERRED EMBODIMENT

Figure 1:
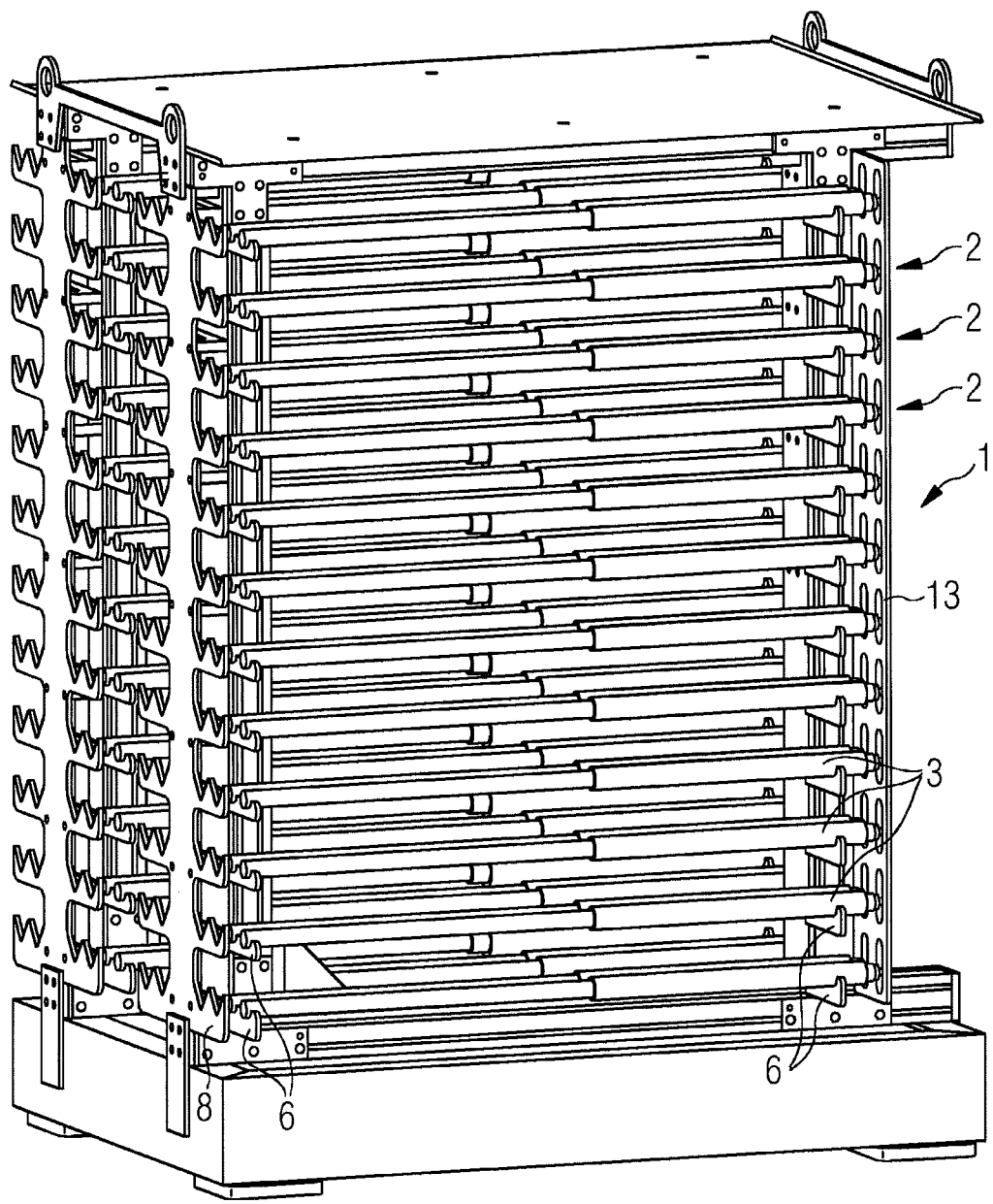
FIGS. 1 and 2 show schematic perspective views of a holding frame.

Reference will now be made in detail to the preferred embodiments of the present invention, examples of which are illustrated in the accompanying drawings, wherein like reference numerals refer to like elements throughout.

Figure 2:
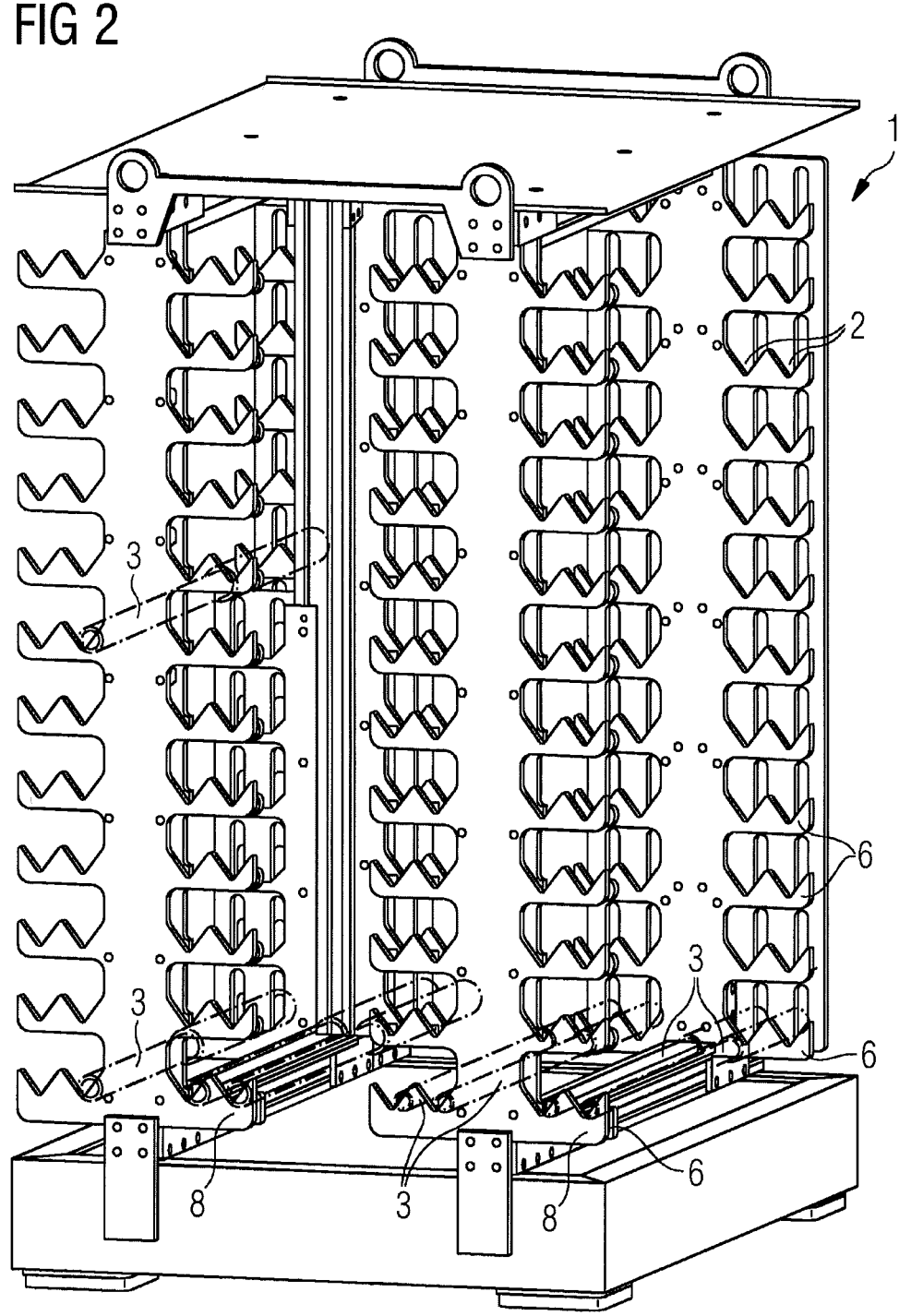

As shown in FIGS. 1 and 2, a holding frame 1 has a plurality of bearing points 2. The bearing points 2 as shown in FIGS. 1 and 2 are arranged in a two-dimensional grid. Alternatively the bearing points 2 could be arranged in a one-dimensional grid. Even an irregular arrangement of the bearing points 2 is theoretically possible. The critical factor is that the bearing points 2 are at defined locations.

Figure 3:
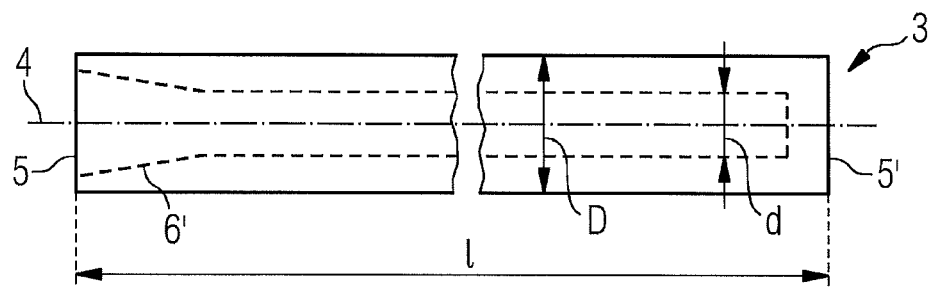
FIG. 3 shows a schematic cross-sectional view of a probe.

The bearing points 2 are each designed to accommodate a (single) metallurgical probe 3. Such probes 3 will be familiar to persons skilled in the art. They are used, for example, to take samples of metal melts or to measure the temperature of such melts. Possible molten metals are in particular iron, steel, copper and aluminum. Other metals are also possible. FIG. 3 shows a typical probe 3 in cross section.

As shown in FIG. 3, the probe 3 is of tubular design. It has a probe longitudinal axis 4 along which it extends. A length l of the probe 3 is often in the order of 1 to 2 m. An outside diameter D of the probe is often in the order of approximately 2.5 to 5 cm.

The probe 3 is internally hollow. It generally has an inside diameter d of 12 to 20 mm, e.g. 16.5 to 17.0 mm. The probe 3 has two end faces 5, 5'. The probe 3 is open on an end face 5—hereinafter referred to as the open end face 5. The probe is closed on the other end face 5'—hereinafter referred to as the closed end face 5'.

Preferably—but not necessarily—the probe 3 is flared at its open end face 5 as shown in FIG. 3. A corresponding flaring 6' can in particular be funnel-shaped.

The time when the probe 3 is flared can be determined as required. For example, the flaring can take place as early as the manufacturing stage of the probe 3. Alternatively, it can take place at a later stage. The critical factor is that the probe 3 is introduced into the probe 3 prior to placement of the probe 3 in one of the bearing points 2 of the holding frame 1, i.e. prior to the bearing point 2 being fitted with the respective probe 3.

Figure 4:
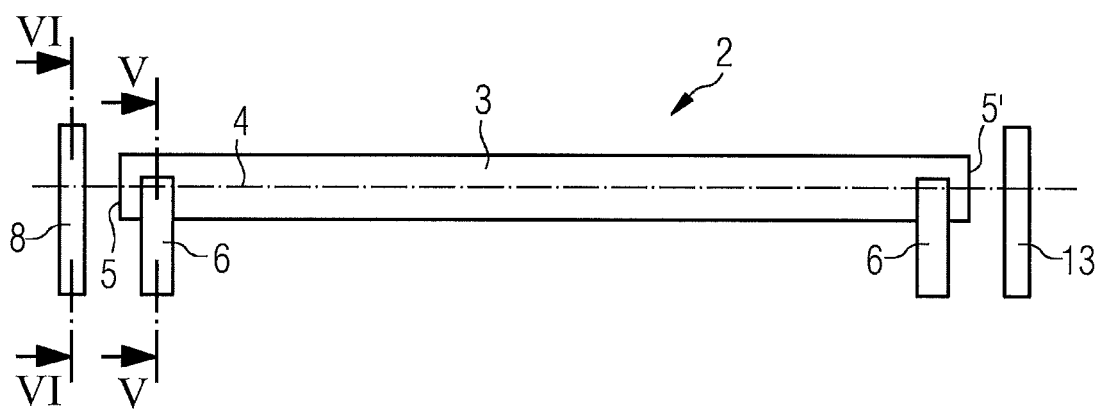
FIG. 4 shows a schematic side view of a bearing point.

FIG. 4 schematically illustrates one of the bearing points 2 of the holding frame 1, wherein the bearing point 2 shown is fitted with a probe 3. The corresponding bearing point 2 has therefore already been loaded. The bearing point 2 has been fitted with the probe 3 such that the open end face 5 thereof faces a predetermined insertion direction.

Figure 5:
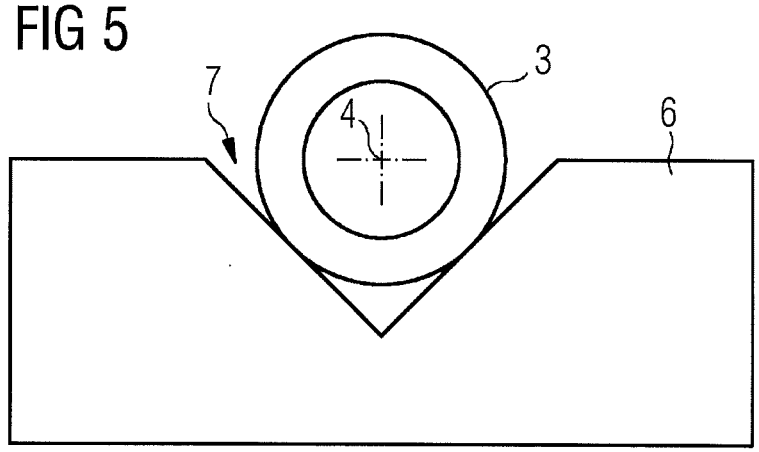
FIG. 5 shows a section along a line V-V in FIG. 4.

As shown in FIG. 4, the bearing point 2 has probe centering elements 6 by which the probe 3 is held in the bearing point 2 in a predetermined position when viewed transversely with respect to the probe longitudinal axis 4. This position will hereinafter be referred to as the probe position. The probe centering elements 6 can be implemented, for example, as steel crosspieces which—see FIG. 5—have a V-shaped (or alternatively e.g. a U-shaped or Y-shaped) recess 7 on their upper side. The probe centering elements 6 could also be implemented, for example, as slots wherein the width thereof corresponds to the outside diameter D of the probe 3.

As shown in FIG. 4, two such probe centering elements 6 are present. However, any number of probe centering elements 6 can be provided. As a minimum, a single probe centering element 6 must be present. Alternatively, three, four, five, etc. probe centering elements 6 could be present.

As shown in FIG. 4, the bearing point 2 additionally has a contact rod centering device 8. The contact rod centering device 8 is designed such that one end 9 of a contact rod 10 can be inserted into it—see FIGS. 6 and 7. The insertion of the end 9 of the contact rod 10 into the contact rod centering device 8 takes place in an insertion direction. The insertion direction—see the arrow in FIG. 8—is transversal with respect to the probe longitudinal axis 4, as can be seen from FIGS. 6 to 8. As shown in FIG. 8, insertion is effected by a holding and movement apparatus 11 which holds the contact rod 10 in a holding area 12 of the contact rod 10. The holding and movement apparatus 11 according to FIG. 8 is implemented as a robotic arm. This design is possible and preferred, but not obligatory. The distance between the holding area 12 of the contact rod 10 and the end 9 of the contact rod 10 is often 1 m or more.

Figure 7:
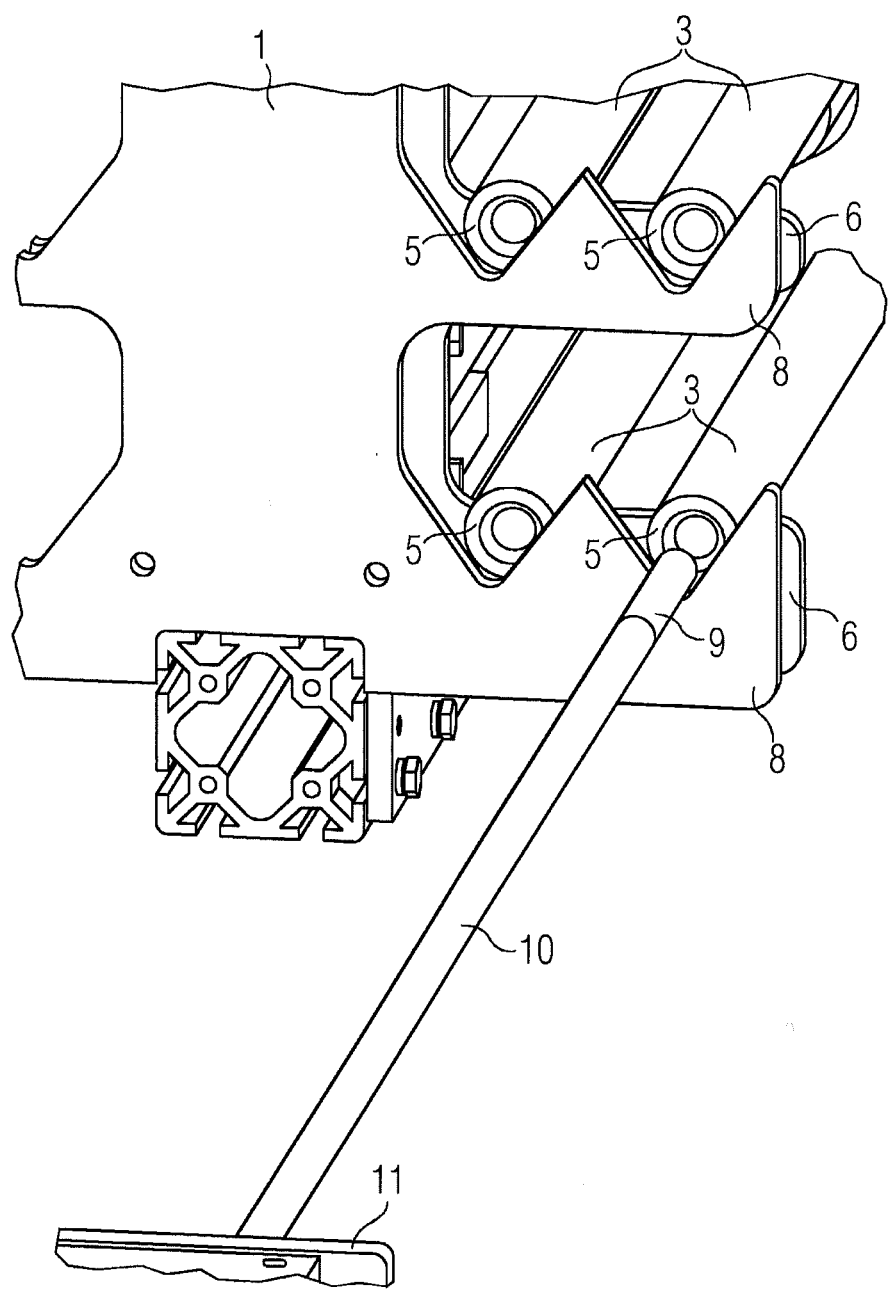
FIG. 7 shows a perspective view of FIG. 6.
Figure 9:
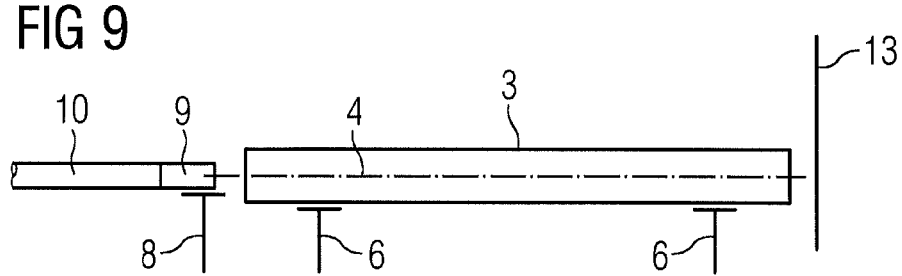

As can be seen from FIGS. 6 to 8, the insertion direction runs from top to bottom. In principle, however, it can run in any direction. The critical factor is that the end 9 of the contact rod 10 is inserted into the contact rod centering device 8 in the insertion direction until the end 9 of the contact rod 10 is positioned at a predetermined contact rod position when viewed transversely with respect to the probe longitudinal axis 4 as a result of insertion into the contact rod centering device 8. The contact rod position—see in particular FIGS. 6 and 7—is selected such that the end 9 of the contact rod 10 is exactly or sufficiently accurately opposite the open end face 5. This position of the end 9 of the contact rod 10 is shown schematically in FIG. 9. The contact rod 10 is therefore next moved—see FIG. 10—by the holding and movement apparatus 11 in the direction of the probe longitudinal axis 4 and thereby inserted into the probe 3.

It is possible that, during the insertion of the end 9 of the contact rod 10, the probe 3 is held in the probe centering elements 6 by its own weight and frictional forces. However, as shown in FIG. 4, on its side opposite the contact rod centering device 8 with respect to the probe 3, the bearing point 2 has a stop 13 for the probe 3. In this case, although the probe 3 can possibly be displaced a small distance by the insertion of the end 9 of the contact rod 10 into the probe 3 until the closed end face 5' of the probe 3 is pressed against the stop 13, any further displacement of the probe 3 in the direction of the probe longitudinal axis 4 will be prevented by the stop 13.

Figure 10:
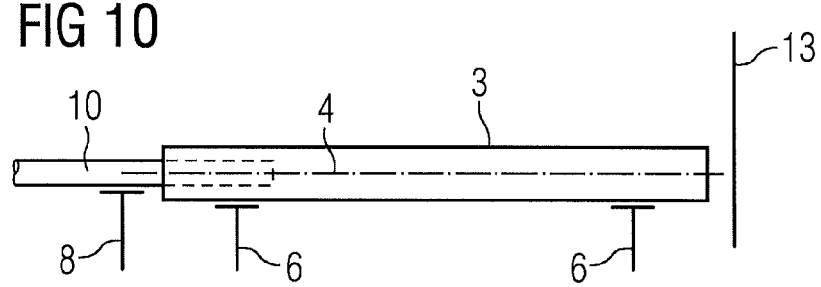
FIG. 10 shows the probe and the contact rod in a partially inserted state of the contact rod.
Figure 11:
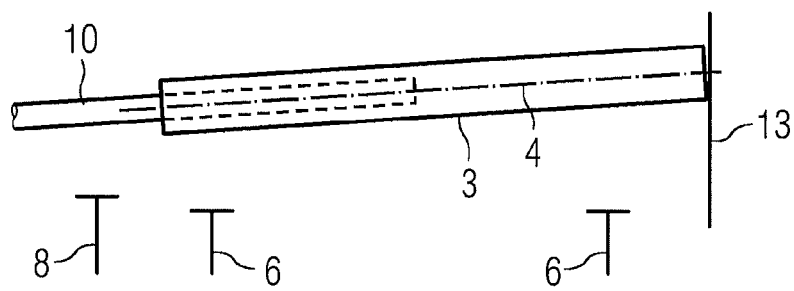
FIG. 11 shows the probe and the contact rod in a raised state of the contact rod, FIG. 12 schematically illustrates a contact rod centering device with the end of the contact rod inserted.

It is conceivable for the contact rod 10 to be immediately inserted completely into the probe 3. Preferably, however, when it is moved in the direction of the probe longitudinal axis 4, the contact rod 10 is initially only partially inserted into the probe 3, e.g. by 10 to 25% of the full insertion length. This state is shown in FIG. 10. The contact rod 10 (and with it the probe 3) is then moved out of the predetermined contact rod position counter to the insertion direction. This state is schematically illustrated in FIG. 11. Only in this state is the contact rod 10 completely inserted into the probe 3. It is also possible for the further insertion of the contact rod 10 into the probe 3 to be carried out incrementally. Alternatively, insertion by the entire insertion length can take place in a second step.

Figure 12:
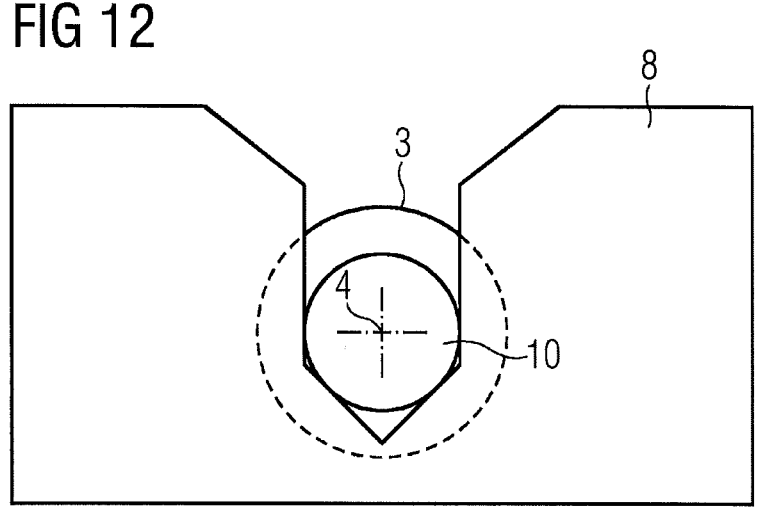

In order to ensure the appropriate positioning of the end 9 of the contact rod 10 in the contact rod centering device, the contact rod centering device 8 can be implemented in various ways. In particular, it is possible that the contact rod centering device 8 is implemented as an essentially V-shaped (alternatively e.g. U-shaped) channel, as shown in FIGS. 6 and 7. However, alternative designs are possible, e.g. Y-shaped, as shown in FIG. 12.

Figure 13:
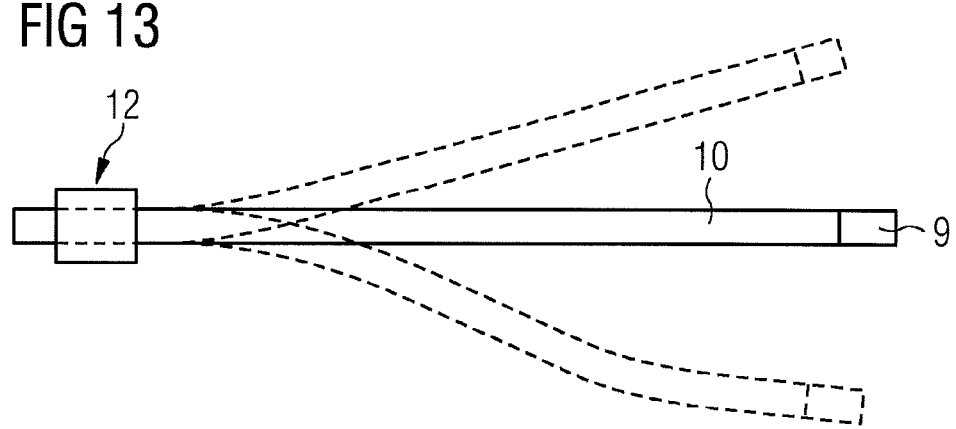
FIG. 13 shows the contact rod in an unbent state and in a bent state, and FIGS. 14 and 15 schematically illustrate the insertion of the end of the contact rod into a contact rod centering device.
Figure 14:
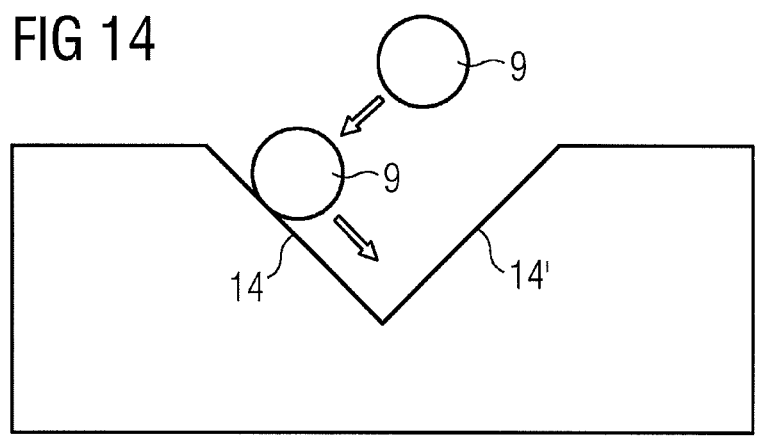

As already mentioned, it can happen that the contact rod 10 is plastically deformed. In this case the contact rod 10 no longer possesses its ideal shape, which is represented as a solid line in FIG. 13, but is bent. Possible deflections are represented—heavily exaggerated—by dashed lines in FIG. 13. In order to reliably ensure that the end 9 of the contact rod 10 is in the contact rod position at the start of insertion into the probe 3, it is possible for a force required for inserting the end 9 of the contact rod 10 to be measured during insertion of the end 9 of the contact rod 10 into the contact rod centering device 8. For example, a motor current or a motor torque of a drive of the holding and movement apparatus 11 can be measured. In this case the attainment of the predetermined contact rod position can be detected on the basis of the force. For example, as shown in FIG. 14, the end 9 of the contact rod 10 can first be advanced at right angles to a first edge 14 of the contact rod centering device 8 onto the edge 14. The reaching of the edge 14 can be detected, for example, by an increase in the electric current required for moving the contact rod 10. The end 9 of the contact rod 10 can then be moved onto a second edge 14' of the contact rod centering device 8 by traversing along the edge 14 until the end 9 of the contact rod 10 lies against the second edge 14' of the contact rod centering device 8. Once again the reaching of the second edge 14' can be detected by a corresponding increase in the motor current. Alternatively, the end 9 of the contact rod 10 can be traversed onto the two edges 14, 14' one after the other and the reaching of the edge 14, 14' detected in each case, the end 9 of the contact rod 10 being held apart from the respective other edge 14', 14 during the two traversing movements. This makes it possible to ascertain—in two dimensions—the degree to which the contact rod 10 is bent.

Figure 15:
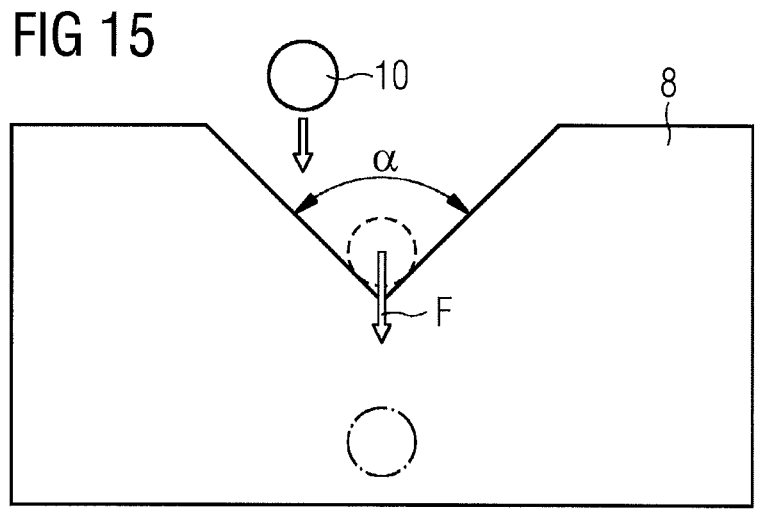

Alternatively, the following procedure is possible: a guide funnel formed by the contact rod centering device 8 is relatively steep, as illustrated in FIG. 15. As shown in FIG. 15, the aperture angle α of the guide funnel is generally max. 90°. The insertion direction corresponds approximately to the angle bisector. If the contact rod 10 were not bent, the position of the end 9 of the contact rod 10 would be unambiguously determined—within narrow limits—by the position of the holding and movement apparatus 11. In particular, an ideal position exists in which the unbent contact rod 10 is held such that the end 9 of the unbent contact rod 10 is (exactly) positioned in the contact rod position. This position of the end 9 of the contact rod 10 is indicated by a dashed line in FIG. 15.

However, the contact rod 10 is not only moved to said ideal position, but beyond it. If the contact rod 10 were unbent and if the contact rod centering device 8 were not present, the end 9 of the contact rod 10 would be in a position indicated by the dash-dotted line in FIG. 15. If the contact rod 10 is unbent and the contact rod centering device 8 is present, the contact rod 10 will therefore be positioned in the desired contact rod position by the contact rod centering device 8, the contact rod 10 being elastically deformed. A bending force F with which the end 9 of the contact rod 10 is held in the desired contact rod position is therefore exerted.

Due to the fact that the contact rod 10 may be bent, it is not known to what extent the end 9 of the contact rod 10 is plastically offset. However, a maximum offset is known. It is therefore merely necessary to ensure that the degree to which the end 9 of the contact rod 10 is moved beyond the ideal position is selected larger than the maximum offset. In this case it is always ensured that the end 9 of the contact rod 10 is pressed against the contact rod centering device 8 in the desired contact rod position. The deflection of the contact rod occurring is only elastic and therefore uncritical.

The present proposed method and device have many advantages. In particular, it is possible to make the holding frame 1 a rigid structure—i.e. without moving parts, without actuators, without control device, etc.—yet nevertheless insert the end 9 of the contact rod 10 safely and reliably into the probe 3. The same applies to an individual bearing point 2. Maintenance in respect of the holding frame 1 or the bearing points 2 is therefore completely eliminated. It is merely necessary to occasionally fit the bearing points 2 with new probes 3. This fitting can be done quickly and easily using either an automated or manual procedure for the fitting process.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV,* 69 USPQ2d 1865 (Fed. Cir. 2004).

The invention claimed is:

1. A method for inserting a contact rod into a metallurgical probe which has a probe longitudinal axis and an open end face, the method comprising:
    fitting the probe within a bearing point such that the open end face of the probe faces a predetermined contact rod position;
    using probe centering elements to hold the probe at the bearing point in a predetermined probe position when viewed transversely with respect to the probe longitudinal axis;
    using a holding and movement apparatus to hold the contact rod in a holding area;
    inserting an end of the contact rod into a contact rod centering device by moving the contact rod in an insertion direction running transversely with respect to the probe longitudinal axis, the contact rod being moved until the end of the contact rod is positioned at the predetermined contact rod position when viewed transversely with respect to the probe longitudinal axis, the end of the contact rod being opposite the open end face of the probe when the contact rod is at the predetermined contact rod position; and
    after inserting the end of the contact rod into the contact rod centering device, moving the contact rod in a direction of the probe longitudinal axis to thereby insert the contact rod into the probe.

2. The method as claimed in claim 1, wherein
    the contact rod is a bent rod,
    an ideal position is defined such that if the contact rod were unbent, the contact rod would have to be moved in the insertion direction to the ideal position so that the end of the contact rod would be positioned at the predetermined contact rod position when viewed transversely with respect to the probe longitudinal axis, and
    the bent rod is moved in the insertion direction to beyond the ideal position.

3. The method as claimed in claim 2, wherein
    while inserting the end of the contact rod into the contact rod centering device, a force required for insertion is measured, and
    the predetermined contact rod position is detected based on the force.

4. The method as claimed in claim 1, wherein
    while inserting the end of the contact rod into the contact rod centering device, a force required for insertion is measured, and
    the predetermined contact rod position is detected based on the force.

5. The method as claimed in claim 1, wherein
    the contact rod, when moved in the direction of the probe longitudinal axis, is initially only partially inserted into the probe,
    after the contact rod is partially inserted into the probe, the contact rod is moved in a direction counter to the insertion direction, and
    after moving the contact rod in the direction counter to the insertion direction, the contact rod is fully inserted into the probe.

6. The method as claimed in claim 1, wherein the open end face of the probe is flared.

7. The method as claimed in claim 6, wherein the open end face is flared prior to fitting the probe within the bearing point.

8. The method as claimed in claim 6, wherein the open end face is flared with a funnel-shaped flare.

9. The method as claimed in claim 1, wherein the holding and movement apparatus is as a robotic arm.

10. A bearing point for a metallurgical probe which has a probe longitudinal axis and an open end face, comprising:
    probe centering elements to hold the probe in a predetermined probe position in the bearing point when viewed transversely with respect to the probe longitudinal axis; and
    a contact rod centering device into which an end of a contact rod is inserted by holding the contact rod in a holding area of the contact rod using a holding and movement apparatus and by moving the contact rod in an insertion direction running transversely with respect to the probe longitudinal axis, the contact rod being moved until the end of the contact rod, as a result of insertion into the contact rod centering device, is positioned at a predetermined contact rod position when viewed transversely with respect to the probe longitudinal axis.

11. The bearing point as claimed in claim 10, wherein the bearing point has a stop on a side opposite to the contact rod centering device with respect to the probe longitudinal axis, the stop preventing the probe from being displaced in a direction of the probe longitudinal axis.

12. A holding frame having a plurality of bearing points respectively for a plurality of metallurgical probes, each having a probe longitudinal axis and an open end face, each bearing point comprising:
    probe centering elements to hold the respective probe in a predetermined probe position in the bearing point when viewed transversely with respect to the probe longitudinal axis; and
    a contact rod centering device into which an end of a contact rod is inserted by holding the contact rod in a holding area of the contact rod using a holding and movement apparatus and by moving the contact rod in an insertion direction running transversely with respect to the probe longitudinal axis, the contact rod being moved until the end of the contact rod, as a result of insertion into the contact rod centering device, is positioned at a predetermined contact rod position when viewed transversely with respect to the probe longitudinal axis.

13. The holding frame as claimed in claim 12, wherein the bearing points are arranged in a two-dimensional grid.

\* \* \* \* \*